US00PP15113P2

(12) United States Plant Patent
Strope

(10) Patent No.: US PP15,113 P2
(45) Date of Patent: Aug. 24, 2004

(54) PETUNIA PLANT NAMED 'BALRUFIMVEIN'

(50) Latin Name: *Petunia×hybrida*
Varietal Denomination: Balrufimvein

(75) Inventor: Kerry Strope, Jefferson City, MO (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/736,727

(22) Filed: Dec. 16, 2003

(51) Int. Cl.[7] ..... A01H 5/00
(52) U.S. Cl. ..... Plt./356
(58) Field of Search ..... Plt./356, 263

*Primary Examiner*—Kent Bell
(74) *Attorney, Agent, or Firm*—Wood, Phillips, Katz, Clark & Mortimer

(57) ABSTRACT

A new and distinct Petunia plant named 'Balrufimvein' characterized by its double purple-colored flowers with darker purple veins, dark green-colored leaves, and a mounded and trailing growth habit.

1 Drawing Sheet

Latin name of the genus and species of plant claimed: *Petunia×hybrida.*
Variety denomination: 'Balrufimvein'.

BACKGROUND OF THE INVENTION

The present invention comprises a new and distinct cultivar of Double Petunia plant botanically known as *Petunia×hybrida* and hereinafter referred to by the cultivar name 'Balrufimvein'.

The new petunia was developed by the inventor through a controlled breeding program during October 2000 at Arroyo Grande, Calif. The objective of the breeding program was the development of Petunia cultivars with large, fully double flowers of unique colors and vigorous mounded and trailing growth habits.

The female parent of 'Balrufimvein' was the proprietary *Petunia×hybrida* breeding selection designated 539A, not patented, which exhibits a semi-trailing habit, dark green-colored foliage, and single pink/white bi-color flowers. The male parent of 'Balrufimvein' was the Petunia cultivar Pricilla (not patented) which exhibits a semi-trailing habit, dark green-colored foliage, and fragrant, double, pale purple-colored flowers with darker purple-colored veins. The new cultivar was discovered and selected as a single flowering plant within the progeny of the above stated cross-pollination during March 2001 in a controlled environment at Arroyo Grande, Calif.

Asexual reproduction of the new cultivar by terminal stem cuttings taken since March 2001 at Arroyo Grande, Calif. and West Chicago, Ill., has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variation in genotype.

It was repeatedly found that the cultivar of the present invention:

1 Exhibits double purple-colored flowers with distinct darker purple venation.

2 Forms dark green-colored foliage.

3 Exhibits a good basal branching character.

4 Exhibits a vigorous mounded and trailing growth habit.

Plants of the new cultivar differ from plants of the female patent primarily in flower form and from the male parent primarily in flower color.

Of the many Petunia cultivars known to the inventor, the most similar to 'Balrufimvein' is the cultivar Kirimaji Double Purple (U.S. Plant Pat. No. 14,283). However, in side-by-side comparisons, flowers of the new cultivar are a lighter purple color than flowers of the cultivar Kirimaji Double Purple.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the color of 'Balrufimvein'. The plants were grown for 12 weeks in a greenhouse at West Chicago, Ill.

DETAILED BOTANICAL DESCRIPTION

Figure 1:
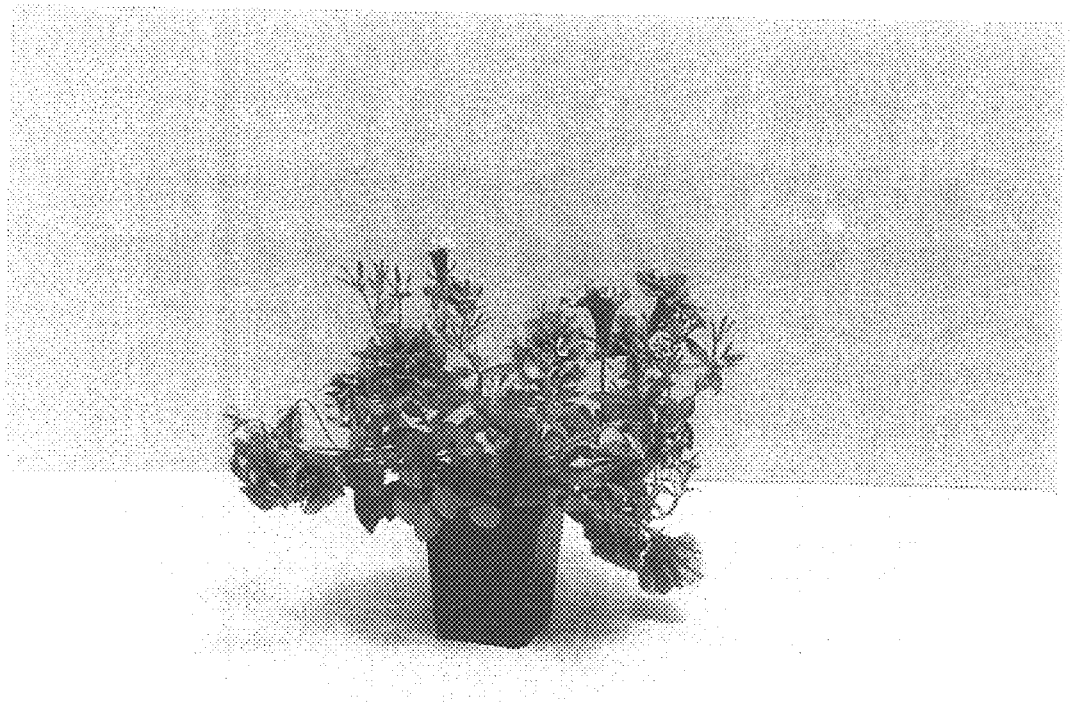
FIG. 1 illustrates a side view of the overall growth and flowering habit of 'Balrufimvein'.
Figure 2:
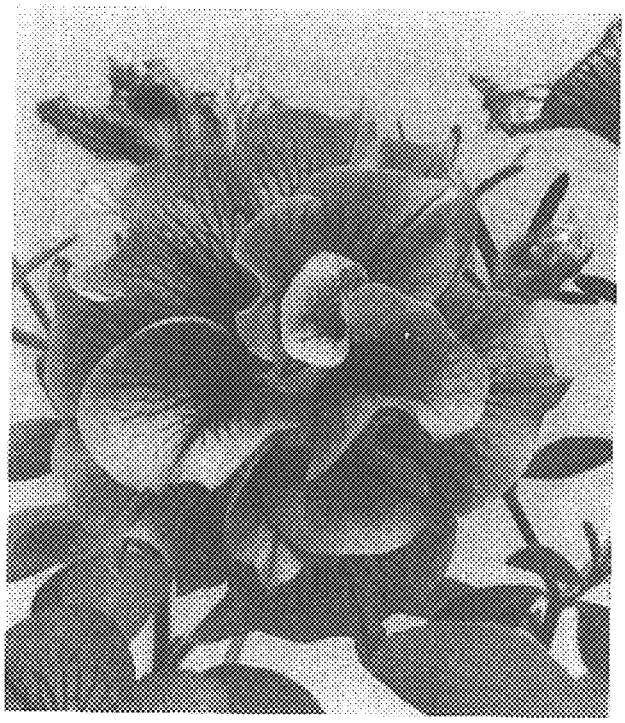
FIG. 2 illustrates a close-up view of a single flower of 'Balrufimvein'.

The chart used in the identification of colors described herein is The R.H.S. Colour Chart of The Royal Horticultural Society, London, England, 1995 edition, except where color terms of ordinary significance are used. The color values were determined on Oct. 15, 2003. The readings were taken between 1:00 and 3:00 p.m. under natural daylight conditions.

Plants used for the following descriptions and measurements were grown in 10 cm pots for 12 weeks from rooted cuttings. The plants were produced from cuttings taken from stock plants and grown in a double polycarbonate-covered greenhouse under conditions comparable to those used in commercial practice. The plants were grown using a soilless growth medium with greenhouse temperatures maintained at approximately 55°–75° F. (13°–24° C.) during the day and approximately 50°–60° F. (10°–16° C.) during the night. Greenhouse light levels of 5,000–8,000 footcandles were maintained during the day.

Botanical classification: *Petunia×hybrida* cultivar Balrufimvein.

Parentage:

*Female parent.*—Proprietary *Petunia×hybrida* breeding selection designated 539A (not patented).

*Male parent.*—Petunia cultivar Pricilla (not patented).

Propagation:

*Type cutting.*—Terminal stem.

*Time to initiate roots.*—Approximately 6 to 9 days.

*Time to produce a rooted cutting.*—Approximately 21 to 30 days.

*Root description.*—Fibrous.

*Rooting habit.*—Freely branching.

Plant description:

*Crop time.*—Approximately 6 to 8 weeks are required to produce a finished plant from rooted cuttings.

*Habit of growth.*—Vigorous and freely branching. Pinching improves basal branching.

*Form.*—Initially upright, becoming cascading as it matures.

*Plant height.*—A mature plant, 12 weeks after the planting of a rooted cutting, commonly measures approximately 16.2 cm from top of soil to top of plant plane.

*Plant diameter* (*area of spread*).—Approximately 46.3 cm.

*Lateral branches.*—Quantity: An average of 5 branches per plant develop after pinching. Length: Approximately 22.4 cm. Diameter: Approximately 2 mm. Texture: Densely pubescent. Color: 144A. Internode length at the middle of the branch: Approximately 2.8 cm.

*Foliage.*—Type: Simple. Arrangement: Alternate. Shape: Ovate. Margin: Entire, pubescent. Apex: Broadly acute. Base: Attenuate. Angle to stem: Acute. Texture: Upper and lower surfaces: Densely pubescent. Quantity of leaves per lateral branch: Approximately 10. Leaf length: Approximately 4.1 cm. Leaf width: Approximately 2.1 cm. Color of upper surface of mature foliage: Slightly darker than 146A. Color of lower surface of mature foliage: Closest to 146B. Both upper and lower surfaces have pinnate venation closest to N144D. Petiole length: Approximately 7 mm. Petiole diameter: Approximately 2 mm. Petiole color: Closest to 144A.

Flowering description:

*Flowering habit.*—Freely flowering with 1 flower and 2 buds per lateral branch.

*Natural flowering season.*—Year round in greenhouse environment and from spring through fall in outdoor garden.

*Lastingness of individual bloom.*—Approximately 6–10 days.

Flower description:

*Type.*—Double, solitary, salverform, indeterminate and persistent. Fragrance: Pungent.

*Size.*—Length (height): Approximately 5.5 cm. Diameter: Approximately 6.6 cm.

*Flower bud.*—Shape: Ovate, elongating as it matures. Length at first color: Approximately 3.9 cm. Diameter at first color: Approximately 1.4 cm. Color: 144D with venation of 79A.

*Corolla.*—Approximately 13 petals with the outer whorl of five petals fused to form corolla tube. Petal shape: Obovate. Petal apex: Mucronate. Petal margin: Entire, undulate. Petal texture: Glabrous. Petal length from throat: 3.5 cm. Petal width at widest point: 3.3 cm. Color of upper surface: Closest to 85C with venation of between N87A and 86A. Color of lower surface: 85D with venation closest to 86A.

*Corolla tube.*—Length: Approximately 2.6 cm. Diameter at distal end: Approximately 1.5 cm. Diameter at proximal end: Approximately 5 mm. Color of outer surface: 79B with venation of 79A. Color of inner surface: 79A with venation of 79A. Texture: Outer surface: Moderately pubescent. Inner surface: Glabrous.

*Peduncle.*—Length: Approximately 4 cm. Diameter: Approximately 1 mm. Strength: Strong. Angle to the stem: Acute. Texture: Densely pubescent. Color: 144A.

*Sepals.*—Five, non-imbricate, fused at base. Length: Approximately 1.8 cm. Width: Approximately 2 mm. Shape: Linear. Apex: Acute. Margin: Entire, pubescent. Texture of both surfaces: Densely pubescent. Color of the upper and lower surfaces: 138A.

*Reproductive organs.*—Stamen quantity: Approximately 16. Stamen length: Approximately 2.2 cm. Filament length: Approximately 2 cm. Filament color: 83D. Anther shape: Oval. Anther length: Approximately 3 mm. Anther color: 85A. Pollen amount: Moderate. Pollen color: 94D. Pistil quantity: 1 per flower. Pistil length: Approximately 2.1 cm. Stigma shape: Funnel. Stigma length: Approximately 5 mm. Stigma color: 79A. Style length: Approximately 1.1 cm. Style color: 144D. Ovary size: Approximately 2.5 mm. Ovary color: 145A.

Seed and fruit production: Neither seed nor fruit production has been observed.

Disease and pest resistance: Resistance to pathogens and pests common to petunias has not been observed.

It is claimed:

1. A new and distinct cultivar of Petunia plant named 'Balrufimvein' substantially, as herein shown and described, which:

1. Exhibits double purple-colored flowers with darker purple venation.
2. Forms dark green-colored foliage.
3. Exhibits a good basal branching character.
4. Exhibits a mounded and trailing growth habit.

* * * * *